(12) United States Patent
Lahti et al.

(10) Patent No.: US 8,706,229 B2
(45) Date of Patent: *Apr. 22, 2014

(54) CONNECTOR ASSEMBLY FOR CONNECTING A LEAD AND AN IMPLANTABLE MEDICAL DEVICE

(75) Inventors: Jay Lahti, Shoreview, MN (US); Andrew J. Ries, Lino Lakes, MN (US); Scott Forsythe, Walworth, WI (US)

(73) Assignee: Medtronic, Inc., Minneapolis, MN (US)

( * ) Notice: Subject to any disclaimer, the term of this patent is extended or adjusted under 35 U.S.C. 154(b) by 396 days.

This patent is subject to a terminal disclaimer.

(21) Appl. No.: 12/760,792

(22) Filed: Apr. 15, 2010

(65) Prior Publication Data

US 2010/0197174 A1 Aug. 5, 2010

Related U.S. Application Data

(62) Division of application No. 10/632,026, filed on Jul. 31, 2003, now abandoned.

(51) Int. Cl.
*A61N 1/375* (2006.01)
(52) U.S. Cl.
USPC ............................................................ 607/37
(58) Field of Classification Search
USPC ........... 607/37, 36; 439/909, 827, 733.1, 335, 439/668
See application file for complete search history.

(56) References Cited

U.S. PATENT DOCUMENTS 2,659,876 A * 11/1953 Dupre et al. ................... 439/846
4,445,511 A 5/1984 Cowdery et al.
4,566,660 A * 1/1986 Anscher et al. ............... 248/74.2
4,848,346 A 7/1989 Crawford
5,222,727 A 6/1993 Jacobsen
5,275,620 A 1/1994 Darby et al.
5,730,628 A 3/1998 Hawkins
5,769,671 A * 6/1998 Lim .............................. 439/843
6,198,969 B1 3/2001 Kuzma
6,501,990 B1 12/2002 Sundberg et al.
7,647,111 B2 * 1/2010 Ries et al. ........................ 607/37
7,769,458 B2 * 8/2010 Ries et al. ........................ 607/37

(Continued)

FOREIGN PATENT DOCUMENTS

EP 5 590 756 A2 6/1994

OTHER PUBLICATIONS

Merriam-Webster Online, Online Dictionary, www.webster.com, define "flange".

*Primary Examiner* — Niketa Patel
*Assistant Examiner* — Alyssa M Alter
(74) *Attorney, Agent, or Firm* — Reed A. Duthler

(57) ABSTRACT

A connector assembly for detachably connecting a lead to an implantable medical device and an implantable medical device capable of being detachably connected to a lead that include one or more deflectable connector clip and a housing. The connector clip includes a first arm, a second arm, and a top portion extending between the first arm and the second arm, and is capable of being deflected from a first position, corresponding to a first relative position of the first arm and the second arm, to a second position corresponding to a second relative position of the first arm and the second arm. The housing includes a first member and a second member, the first member formed to be fixedly engaged with the second member to enclose the connector clip within the housing with the one or more connector clip being positioned within one of the first member and the second member.

3 Claims, 8 Drawing Sheets

(56) References Cited

U.S. PATENT DOCUMENTS

| | | |
|---|---|---|
| 2002/0193858 A1 | 12/2002 | Schulman et al. |
| 2004/0093038 A1 | 5/2004 | Biggs et al. |
| 2005/0027325 A1* | 2/2005 | Lahti et al. .................. 607/37 |
| 2005/0027326 A1 | 2/2005 | Ries et al. |
| 2005/0027367 A1 | 2/2005 | Heide et al. |

* cited by examiner

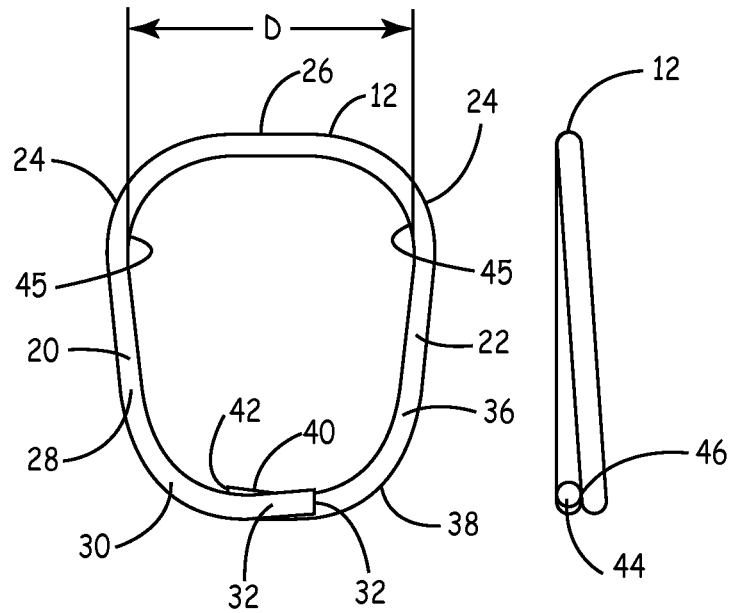
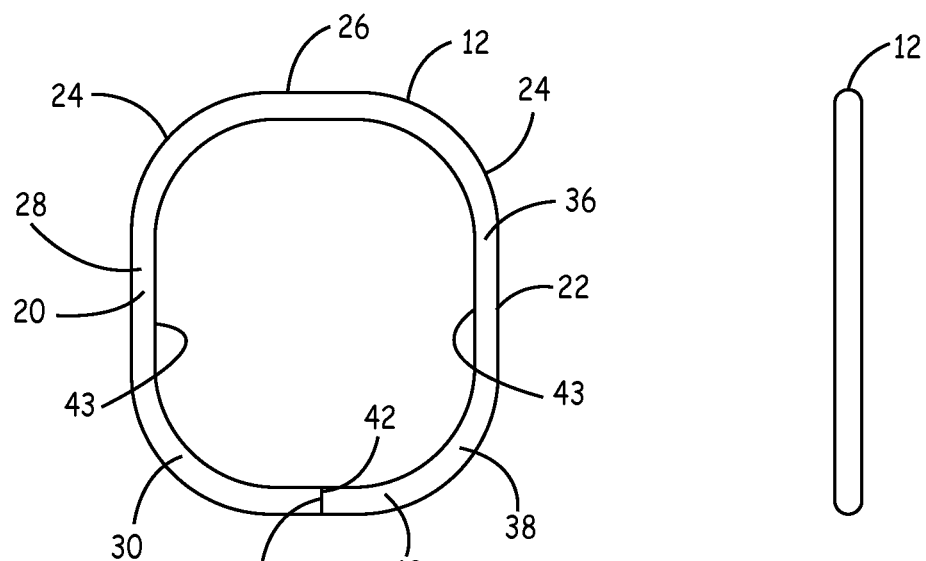

CONNECTOR ASSEMBLY FOR CONNECTING A LEAD AND AN IMPLANTABLE MEDICAL DEVICE

CROSS-REFERENCE TO RELATED APPLICATION

This application is a divisional of U.S. patent application Ser. No. 10/632,026, filed Jul. 31, 2003 entitled "CONNECTOR ASSEMBLY FOR CONNECTING A LEAD AND AN IMPLANTABLE MEDICAL DEVICE", herein incorporated by reference in its entirety.

Cross-reference is also hereby made to commonly assigned related U.S. applications, filed concurrently herewith, U.S. patent application Ser. No. 10/632,028, which is now U.S. Pat. No. 7,647,111, entitled "CONNECTOR ASSEMBLY FOR CONNECTING A LEAD AND AN IMPLANTABLE MEDICAL DEVICE" and U.S. patent application Ser. No. 10/632,058, which is now U.S. Pat. No. 7,769,458, entitled "SMALL FORMAT CONNECTOR CLIP OF AN IMPLANTABLE MEDICAL DEVICE", and U.S. patent application Ser. No. 10/632,027, which is now U.S. Pat. No. 7,164,951, entitled "ELECTRICAL CONNECTOR ASSEMBLY FOR COUPLING MEDICAL LEADS TO IMPLANTABLE MEDICAL DEVICES", incorporated herein by reference in their entirety.

FIELD OF THE INVENTION

The present invention relates to medical leads of implantable medical devices and, more particularly, to a connector assembly of an implantable medical device that facilitates coupling between a lead and circuitry of the implantable medical device.

BACKGROUND

In the medical field, leads are used with a wide variety of medical devices. For example, leads are commonly implemented to form part of an implantable medical device (IMD), such as implantable cardiac pacemakers that provide therapeutic stimulation to the heart by delivering pacing, cardioversion or defibrillation pulses. The pulses can be delivered to the heart via electrodes disposed on the leads, e.g., typically near distal ends of the leads. In that case, the leads may position the electrodes with respect to various cardiac locations so that the pacemaker can deliver pulses to the appropriate locations. Leads are also used for sensing purposes, or both sensing and stimulation purposes.

In addition, leads are used in neurological devices such as deep-brain stimulation devices, and spinal cord stimulation devices. For example, the leads may be stereotactically probed into the brain to position electrodes for deep brain stimulation. Leads are also used with a wide variety of other medical devices including, for example, devices that provide muscular stimulation therapy, devices that sense chemical conditions in a patient's blood, and the like. In short, medical leads may be used for sensing purposes, stimulation purposes, or both.

An IMD typically includes one or more leads, a housing that houses circuitry of the IMD, and a connector block that couples the lead to the circuitry. In particular, the connector block includes electrical contact structures for coupling the lead to circuitry within the housing of the IMD so that therapeutic simulation can be provided through the lead, or sensed conditions can be recorded by the circuitry. One challenge in implementing medical leads in a medical device is the electrical coupling between a respective lead and circuitry of the IMD.

Various connection standards have been developed in order to ensure electrical connections between the IMD circuitry and the lead are acceptable, while also maintaining a sufficient hermetic seal between the connector block and the lead to avoid ingress of body fluids into the housing. These standards continue to evolve to accommodate new lead designs, such as in-line leads that include a plurality of electrical contact areas along axial positions of the lead.

In general, there remains a need for lead connector configurations that are simple to use and inexpensive to fabricate. Improved simplicity can help ensure that physicians can make the electrical connections during implantation of the IMD with minimal concern for electrical coupling malfunction. Reduced fabrication expense can help ensure that patient costs associated with an IMD can be minimized.

BRIEF DESCRIPTION OF THE DRAWINGS

It is to be understood that the foregoing general description and the following detailed description are exemplary and explanatory but are not to be restrictive of the invention. The accompanying drawings which are incorporated in and constitute a part of this invention, illustrate one or more of the embodiments of the present invention, and together with the description, serve to explain the principles of the invention in general terms. Additionally, other features which are considered as characteristic for the invention are set forth in the appended claims. Advantages and features of the present invention will be readily appreciated as the same becomes better understood by reference to the following detailed description when considered in connection with the accompanying drawings, in which like reference numerals designate like parts throughout the figures thereof and wherein:

FIG. 3A is a plan view of a connector clip utilized in a connector assembly of the present invention in a non-deflected position;

FIG. 3B is a side view of the connector clip of FIG. 3A;

FIG. 3C is a plan view of a connector clip utilized in a connector assembly of the present invention in a partially deflected position;

FIG. 3D is a side view of the connector clip of FIG. 3C;

FIG. 6 is a schematic diagram of a connector assembly according to the present invention inserted within a connector cavity and having a lead connector positioned there through;

DETAILED DESCRIPTION

The present invention relates to an improved connector assembly for detachably connecting and retaining the terminal pin of an electrical lead to an implantable medical device. The invention utilizes one or more resilient connector clips that are in a partially deflected configuration, or partially loaded state, such that a relatively constant force is exerted over the full range of deflection of the spring, and are positioned within a housing. Since only a small deflection of the spring is necessary to create significant force of retention on the inserted terminal pin of the lead, the connector assembly of the present invention allows for ease in inserting the terminal pin of the lead and allows for sufficient force to be exerted on the terminal pin for optimum retention of the lead without damaging it. Furthermore, the connector assembly of the present invention makes efficient use of the axial space on the terminal pin, allowing it to be very compact. Axial space is efficiently used due to the alignment of the spring contact perpendicular to the inserted lead. The connector readily accepts insertion of a terminal pin, without the use of tools, and applies a relatively even force through the connector clips to maintain a constant electrical contact with the electrical lead that is not subject to varying impedance. The connector of the present invention provides the requisite mechanical and electrical connection functions, using fewer components and less labor in implementation, yet providing higher reliability, durability, resistance to breakdown due to reactions with body fluids, a small size, and efficiency in manufacture.

Figure 1:
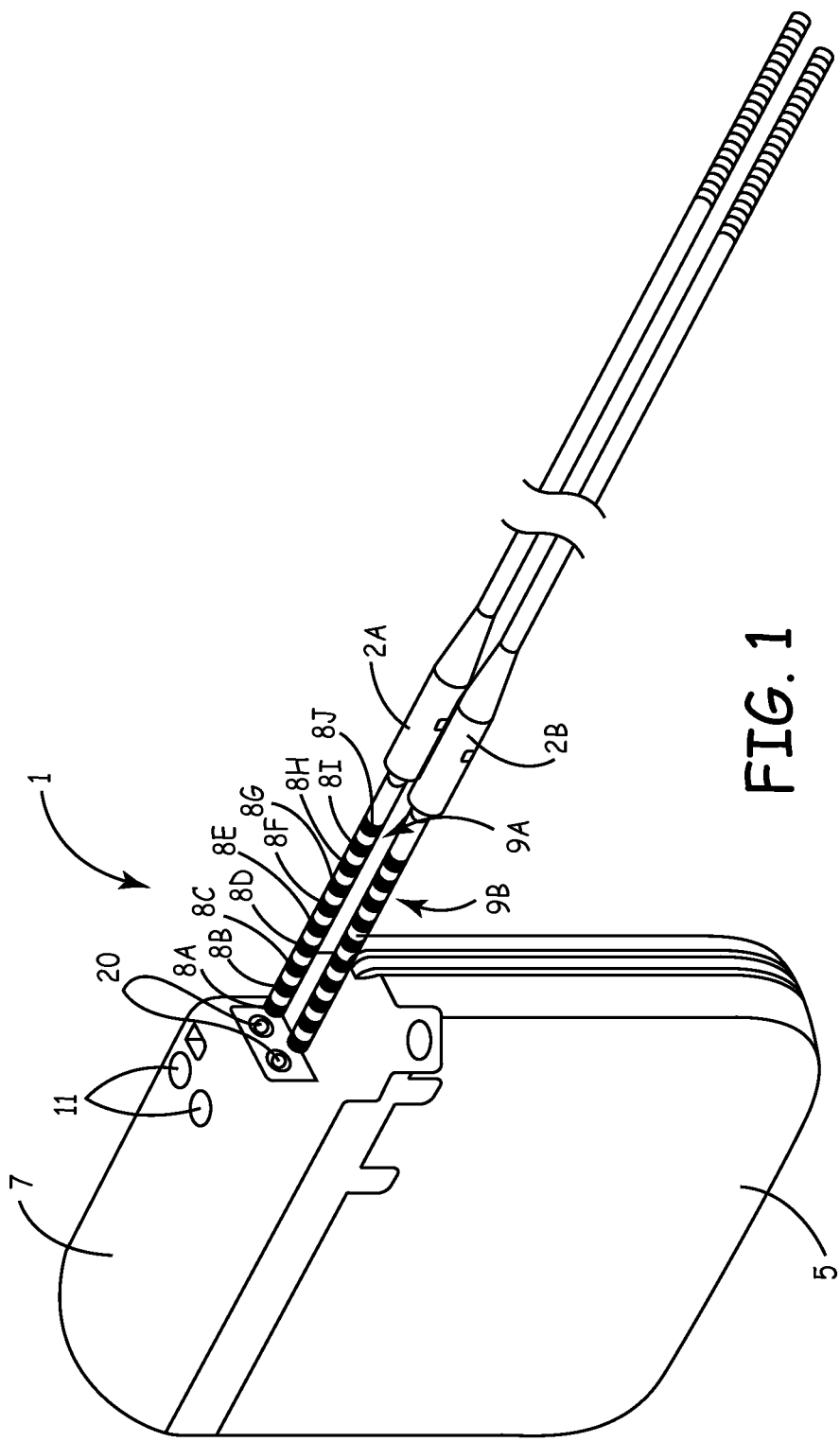
FIG. 1 is a perspective view of an exemplary implantable medical device capable of incorporating a connector assembly according to the present invention.

FIG. 1 is a perspective view of an exemplary implantable medical device capable of incorporating a connector assembly according to the present invention. As illustrated in FIG. 1, an exemplary implantable medical device (IMD) 1 incorporating a connector assembly according to the present invention includes a hermetically sealed, biologically inert housing 5, or "can", that houses IMD circuitry, one or more leads 2A, 2B (collectively leads 2) that can be implanted in a patient, and a connector block 7 that receives proximal ends 9A, 9B of leads 2 to couple leads 2 to the circuitry in housing 5 as leads 2 are inserted within a connector port 3 formed in connector block 7. Once fully inserted within connector block 7, leads 2 are further fixedly positioned within connector block 7 by tightening positioning screws 11 against leads 2.

As illustrated in FIG. 1, the proximal ends 9A and 9B of lead 2A and 2B, respectively, include a plurality of electrical contact areas 8A-8J (collectively contact areas 8). The present invention facilitates electrical coupling to one or more of contact areas 8 within connector block 7. Moreover, the present invention improves such contact for inline configurations like FIG. 1 in which a plurality of electrical contact areas 8 are positioned axially along a length of leads 2. In particular, the present invention allows size reductions of contact areas 8 by improving electrical coupling clips, described below, that electrically interface with contact areas 8 inside connector block 7.

IMD 1 corresponds to any medical device that includes medical leads and circuitry coupled to the medical leads. By way of example, IMD 1 takes the form of an implantable cardiac pacemaker that provides therapeutic stimulation to the heart. Alternatively, IMD 1 may take the form of an implantable cardioverter or an implantable defibrillator, or an implantable cardiac pacemaker-cardioverter-defibrillator. IMD 1 may deliver pacing, cardioversion or defibrillation pulses to a patient via electrodes disposed on distal ends of leads 2. In other words, leads 2 position electrodes with respect to various cardiac locations so that IMD 1 can deliver pulses to the appropriate locations.

Alternatively, IMD 1 corresponds to a patient monitoring device, or a device that integrates monitoring and stimulation features. In those cases, leads 2 include sensors positioned along distal ends of the respective lead for sensing patient conditions. The sensors include, for example, electrical sensors, electrochemical sensors, pressure sensors, flow sensors, acoustic sensors, optical sensors, or the like. In many cases, IMD 1 performs both sensing and stimulation functions.

In still other applications, IMD 1 corresponds to a neurological device such as a deep-brain stimulation device or a spinal cord stimulation device. In those cases, leads 2 are stereotactically probed into the brain to position electrodes for deep brain stimulation, or into the spine for spinal stimulation. In other applications, IMD 1 provides muscular stimulation therapy, blood sensing functions, and the like. In short, IMD 1 corresponds to any of a wide variety of medical devices that implement leads and circuitry coupled to the leads.

As outlined in detail below, connector block 7 of the present invention incorporates various components that improve and simplify electrical coupling between leads 2 and circuitry in housing 5. More specifically, an electrical connector clip provides a conductive interface between a medical lead and IMD circuitry. In addition, various components that assemble with the connector clip to form at least a portion of connector block 7 of IMD 1 are also described. For example, an improved structure having a channel for mating with one or more of leads 2 is designed for use with the connector clip so that biasing of the connector clip can be achieved prior to insertion of one or more leads 2 into the channel. As described below, such biasing allows for ease of insertion of one or more of leads 2 into the channel of the structure that forms at least part of connector block 7. In other words, the connector clip defines a desired amount of insertion force for lead pins inserted into connector block 7.

Figure 2:
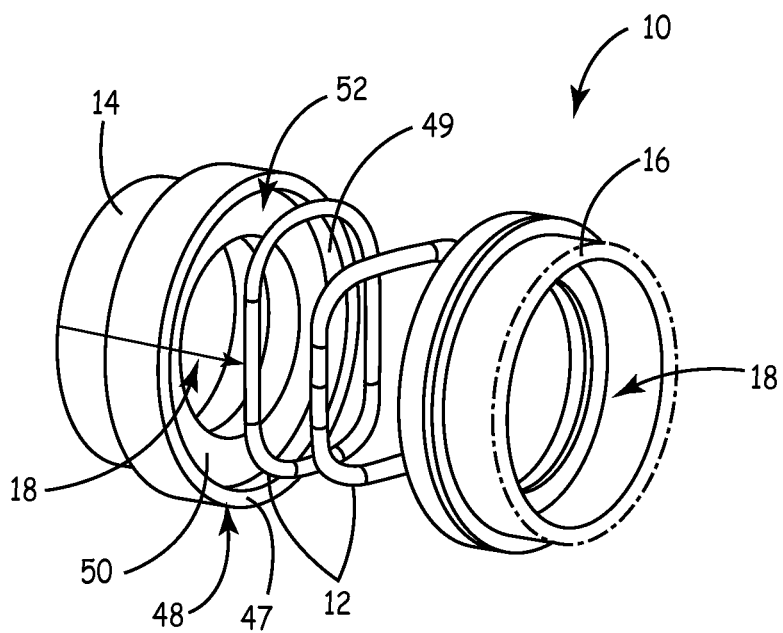
FIG. 2 is an exploded view, in perspective, of an embodiment of a connector assembly according to the present invention.

FIG. 2 is an exploded view, in perspective, of an embodiment of a connector assembly according to the present invention. As illustrated in FIG. 2, according to the present invention, a housing 13 of a connector assembly 10, which is included as a portion of connector block 7 in direct communication with connector port 3, includes a female member 14 and a male member 16. A connector clip 12 is positioned within either female member 14 or male member 16 of housing 13, or both. In addition, more than one connector clip 12 may be positioned within female member 14 or male member 16 or both so that any number of connector clips can be utilized as desired. In the exemplary embodiment illustrated in FIG. 2, each of male member 16 and female member 14 include a connector clip 12 positioned therein, as described below. Connector clip 12 is resilient and electrically conductive, while housing 13 is sealable and electrically conductive. Furthermore, both female member 14 and male member 16 form an aperture 18 extending therethrough for insertion of an electrical lead through housing 13 as the lead is inserted within connector port 3.

Connector clip 12 is may be used both to provide a means of retaining a lead (not shown) in place, and as a means of conducting electricity between contact areas 8 of a terminal pin of the lead, or both functions together in an electrical apparatus such as a pacemaker. Connector clip 12 is preferably prepared from a resilient, high strength, corrosion resistant, biocompatible material, such as tempered stainless steel. However, other materials suitable for such applications may be utilized in forming connector clip 12 employed in the present invention. Connector clip 12 may be stamped or cut from a sheet metal strip or cut and formed from wire stock. Connector clip 12 resembles a wire in form, and may be prepared with a number of differing cross-sections, such as circular or oval, for example, where a cross-section is created by a plane cutting perpendicular to the long axis of the wire.

FIG. 3A is a plan view of a connector clip utilized in a connector assembly of the present invention in a non-deflected position. FIG. 3B is a side view of the connector clip of FIG. 3A. FIG. 3C is a plan view of a connector clip utilized in a connector assembly of the present invention in a partially deflected position. FIG. 3D is a side view of the connector clip of FIG. 3C. As illustrated in FIGS. 3A-3D, connector clip 12 is a single unitary wire formed to generally include a first spring arm 20 and a second spring arm 22. Both spring arm 20 and spring arm 22 include an upper curved portion 24 that together form a top portion 26 of connector clip 12. Spring arm 20 includes a generally straight side portion 28 that extends from upper curved portion 24 to a lower curved portion 30, and a generally straight bottom portion 32 that extends outward from lower curved portion 30 to an end 34 of spring arm 20 that extends inward toward spring arm 22. In the same way, spring arm 22 includes a generally straight side portion 36 that extends from upper curved portion 24 to a lower curved portion 38, and a generally straight bottom portion 40 that extends outward from lower curved portion 38 to an end 42 of spring arm 22 that extends inward toward spring arm 20. As illustrated in FIGS. 3A and 3B, when connector clip 12 is in the relaxed or non-deflected position, spring arm 20 and spring arm 22 are biased inward by the spring action generated at top portion 26 of connector clip so that bottom portion 32 of spring arm 20 and bottom portion 40 of spring arm 22 are offset and adjacent to each other, and a side wall 44 of bottom portion 32 is engaged against a side wall 46 of bottom portion 40. On the other hand, as illustrated in FIGS. 3C and 3D, when connector clip 12 is in a partially deflected position, spring arm 20 and spring arm 22 are deflected outward from the non-deflected position so that side wall 44 of bottom portion 32 is no longer adjacent to and engaged against side wall 46 of bottom portion 40. Rather, in the partially deflected position, spring arm 20 and spring arm 22 are deflected outward so that end 34 of spring arm 20 is positioned adjacent to end 42 of spring arm 22. As a result of the spring force generated by deflection of top portion 26 of connector clip 12, end 34 of spring arm 20 is fixedly engaged against end 42 of spring arm 22 so that connector clip 12 is maintained in the partially deflected position of FIGS. 3C and 3D.

The dimensions of connector clip 12 may vary widely depending upon the size of the lead and the size of the cavity included in the implantable medical device. However, connector assembly 10 according to the present invention, when included within a pacemaker device, for example, will generally include connector clip 12 having a thickness of approximately 0.0100.+−.0.0005 inches, and a distance between top portion 26 and bottom portion 32 of spring arm 20 bottom portion 40 of spring arm 22 of approximately 0.165 inches, and between an inner portion 43 of side walls 28 and 36 of approximately 0.120 inches when connector clip 12 is in the partially deflected position of FIGS. 3C and 3D. When in the non-deflected position of FIGS. 3A and 3B, end 34 of spring arm 20 is spaced approximately 0.030 inches from end 42 of spring arm 22 and a distance D between an inner portion 45 of spring arm 20 where straight side portion 28 meets upper curved portion 24 of spring arm 20 and inner portion 45 of spring arm 22 where straight side portion 36 meets upper curved portion 24 of spring arm 22 is approximately 0.112 inches.

Figure 4:
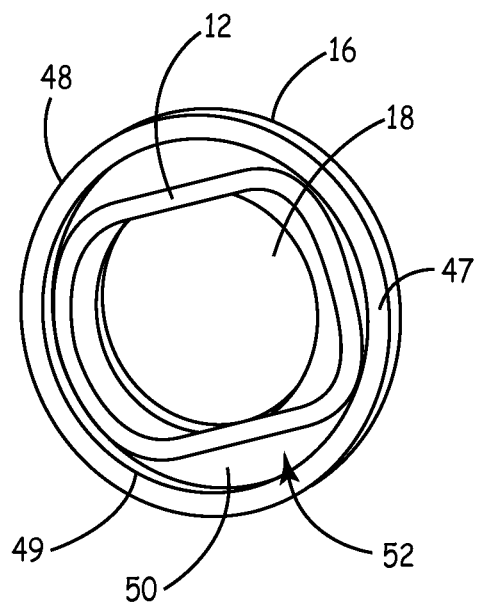
FIG. 4 is a front view of a housing member of a connector assembly according to the present invention having a connector clip, in a partially deflected position, positioned within the housing member.

FIG. 4 is a front view of a housing member of a connector assembly according to the present invention having a connector clip, in a partially deflected position, positioned within the housing member. As illustrated in FIGS. 2 and 4, both female member 14 and male member 16 of housing 13 is formed to position connector clip 12 therein. In particular, both female member 14 and male member 16 are formed to be generally circular in shape, forming a circular central aperture 18 of sufficient size to accept proximal ends 9A or 9B of leads 2A and 2B. Therefore, embodiments of the present invention include aperture 18 having a diameter in a range of approximately 0.05-0.25 inches, although any sized diameter could be chosen. In one embodiment, for example, aperture 18 has a diameter of approximately 0.13 inches. An outer rim of female member 14 and male member 16 forms an annular flange 48 having a top portion 47 that extends outward from a front surface 50 forming aperture 18. A side wall 49 of annular flange 48 and front surface 50 form a recessed portion 52 in which connector clip 12 is positioned while in the partially-deflected position of FIGS. 3C and 3D, with top portion 26 of connector clip 12 positioned against side wall 49 of flange 48. In addition, partially deflected connector clip 12 is positioned within recessed portion 52 so that side portion 28 of spring arm 20 and side portion 36 of spring arm 22 extend over aperture 18, and both lower curved portion 30, straight bottom portion 32 and end 34 of spring arm 20 and lower curved portion 38, straight bottom portion 40 and end 42 of spring arm 22 are spaced a distance from side wall 49 to enable connector clip 12 to be advanced from the partially deflected position to a fully deflected position, described below, when the lead 2 is advanced through housing 13. Once in the desired position within female member 14 and/or male member 16, connector clip 12 is fixedly attached to front surface 50 using known welding techniques such as a laser beam weld for example, along top portion 26 of connector clip 12 and front surface 50

Figure 5A:
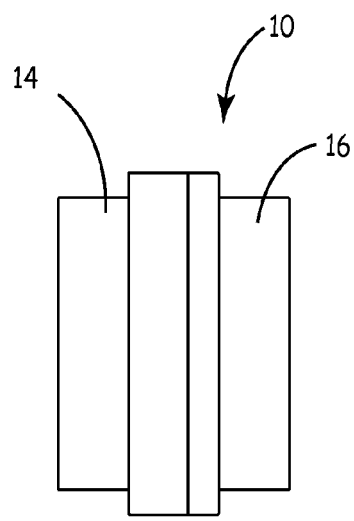
FIG. 5A is a side view of an assembled housing of a connector assembly according to the present invention.
Figure 5B:
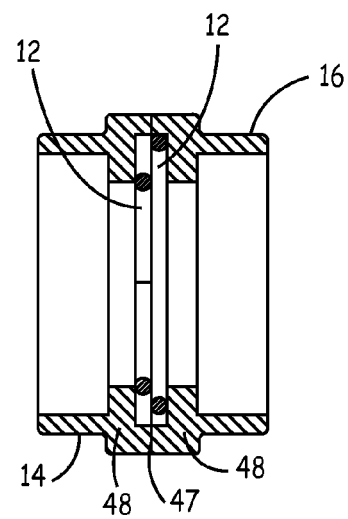
FIG. 5B is a cross-section side view of the assembled housing of the connector assembly of FIG. 5A.

FIG. 5A is a side view of an assembled housing of a connector assembly according to the present invention. FIG. 5B is a cross-section side view of the assembled housing of the connector assembly of FIG. 5A. As illustrated in FIGS. 5A and 5B, once the desired number of connector clips 12 have been positioned within female member 14 and male member 16 of housing 13 as described above, top portion 47 of flange 48 of female member 14 is aligned with and fixedly positioned against top portion 47 of flange 48 of male member 16 using known welding techniques, such as laser beam welding, for example, to form a fully assembled connector assembly 10 that creates a barrier against leakage of fluid through connector assembly 10 into the implantable medical device 1.

Figure 5C:
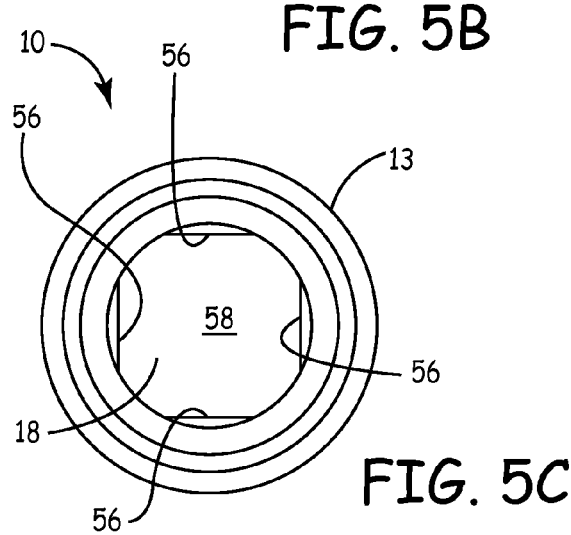
FIG. 5C is a top view of an assembled connector assembly according to the present invention.

Finally, FIG. 5C is a top view of an assembled connector assembly according to the present invention. As illustrated in FIG. 5C, contact points 56 located along spring arms 20 and 22 of connector clip 12 positioned within female member 14 and of connector clip 12 positioned within male member 16 forming housing 13 of assembled connector assembly 10 are visible where spring arm 20 and 22 of connector clip 12 extend within aperture 18 created by housing, with aperture 18 of female member 14 and male member 16 of housing 13 overlapping in fluid communication to form an opening 58 for receiving a lead with spring arm 20 and spring arm 22 in the partially deflected position so that lead comes in contact with spring arm 20 and spring arm 22 at contact points 56. When connector clip 12 is positioned within female member 14 and male member 16 and juxtaposed in a perpendicular manner, as illustrated in FIG. 2, the two connector clips 12 form a square aperture for receiving a lead wherein the midpoint of each side of the square forms a potential contact point 56. While not required to practice the present invention, an embodiment using two, perpendicularly-placed connector clips 12 provides four contact points 56 along the four points of the compass. The placement of two perpendicular connector clips 12 helps to securely contact and retain the contact areas of a lead, as deviation of the lead in any particular direction will naturally be countered by the tension within the connector clips 12. As a result, the connector of the lead may be oriented in any direction around its central axis and function equally well.

Male member 16 and female member 14 of the present invention are preferably prepared from a high strength, corrosion resistant, biocompatible material, such as tempered stainless steel. However, any conductive biocompatible material may be utilized to prepare housing 13 of the present invention. As previously suggested, housing serves to position one or more partially deflected connector clip 12 over aperture 18 to form contact points 56 that come in contact with a lead as the lead is advanced through aperture 18. Generally, housing 13 also serves to conduct electricity from connector clips 12 to another conductor (not shown), which is connected with the electrical apparatus, such as a pacemaker.

Figure 6:
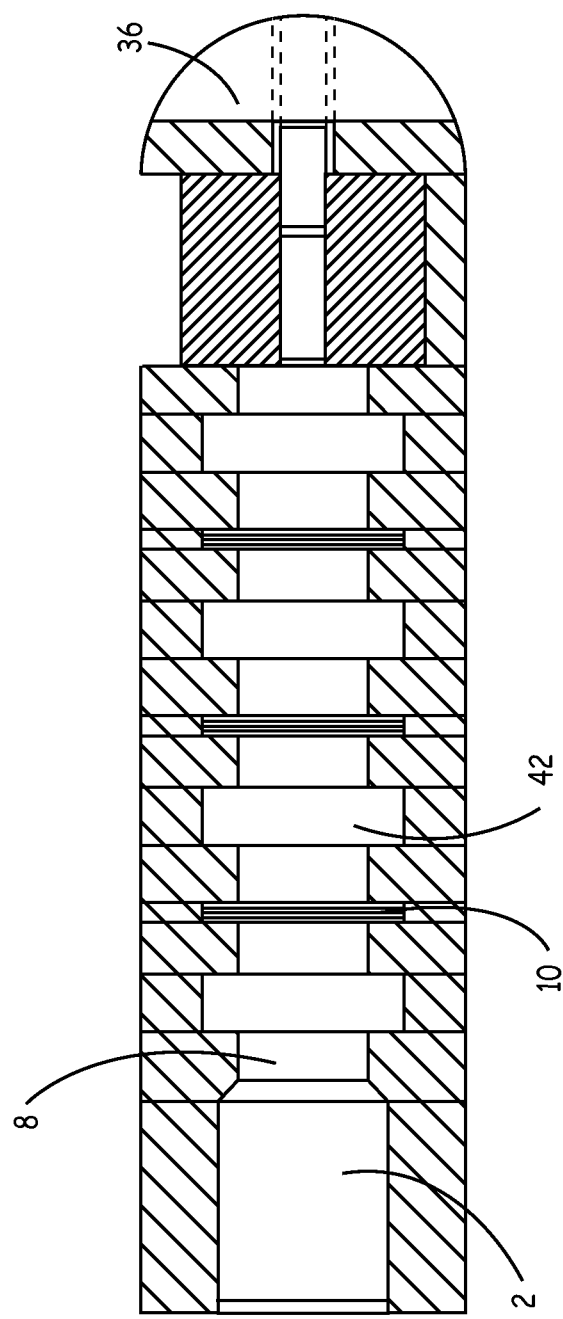

FIG. 6 is a schematic diagram of a connector assembly according to the present invention inserted within a connector cavity and having a lead connector positioned there through. As illustrated in FIG. 6, housing 13 also allows connector assembly 10 to be properly positioned within a connector cavity 36, as illustrated in FIG. 6. While the FIGS. 1-9C illustrate a cylindrical, disc-shaped connector with a circular aperture, neither of these structural features are required for the present invention. For example, if it were desirable to attach a square lead, a square central aperture would be preferred. Furthermore, the overall shape of the connector assembly 10 may deviate from the cylindrical disc illustrated in FIGS. 1-9C without compromising its function.

Prior to use of the present invention, one or more connector clips 12 are placed within housing 13 in the partially deflected position so as to reduce the force required to insert the lead into connector assembly 10, with a portion of each spring arm 20 and 22 projecting over circular aperture 18. After such placement of connector clip 12, connecter assembly 10 is ready to receive and retain an electrical lead.

According to the present invention, the connection of lead 2A or 2B to an electrical device may be accomplished by utilizing one or more of connector assemblies 10 of the present invention. As illustrated in FIG. 6, several of connector assemblies 10 of the present invention may be utilized within a connector cavity 36 forming a portion of connector block 7 that conforms with international standard IS-4 requirements. Use of several connector assemblies 10 provide a greater number of contact points 56, resulting in an even more secure and reliable connection to contact areas 8 of electrical lead 2A or 2B.

Whether one or more connector assemblies 10 of the present invention is utilized, each connector assembly 10 is positioned within connector cavity 36 of a connector region where connector assembly 10 is coupled with wires or other suitable means such that connector assembly 10 is in electrical communication with an electrical source (not shown). The connector region is normally constructed from plastic, silastic, or other electrically non-conductive material, and serves to position connector assembly 10 while preventing undesirable leakage of body fluids or electric current. A wire (not shown) generally runs from connector assembly 10 to the working portion of the apparatus that provides transmission of electrical current, such as electrical pulses. Examples of apparatuses for emitting electrical pulses for use with the present invention may be single or dual chamber pacemakers, antiarrhythmia pacers, defibrillators, cardiomyoplasty stimulators, neurostimulators, and other such devices which emit electrical impulses. Also shown in FIG. 6 are several sealing devices 42, which help assure that body fluids do not leak into and possibly clog and/or corrode the connector 10, the contact areas 8 and the electrical apparatus. Also illustrated in FIG. 6 are several sealing devices 42, which help assure that body fluids do not leak into and possibly clog and/or corrode connector assembly 10, contact areas 8 and the electrical apparatus.

Figure 7:
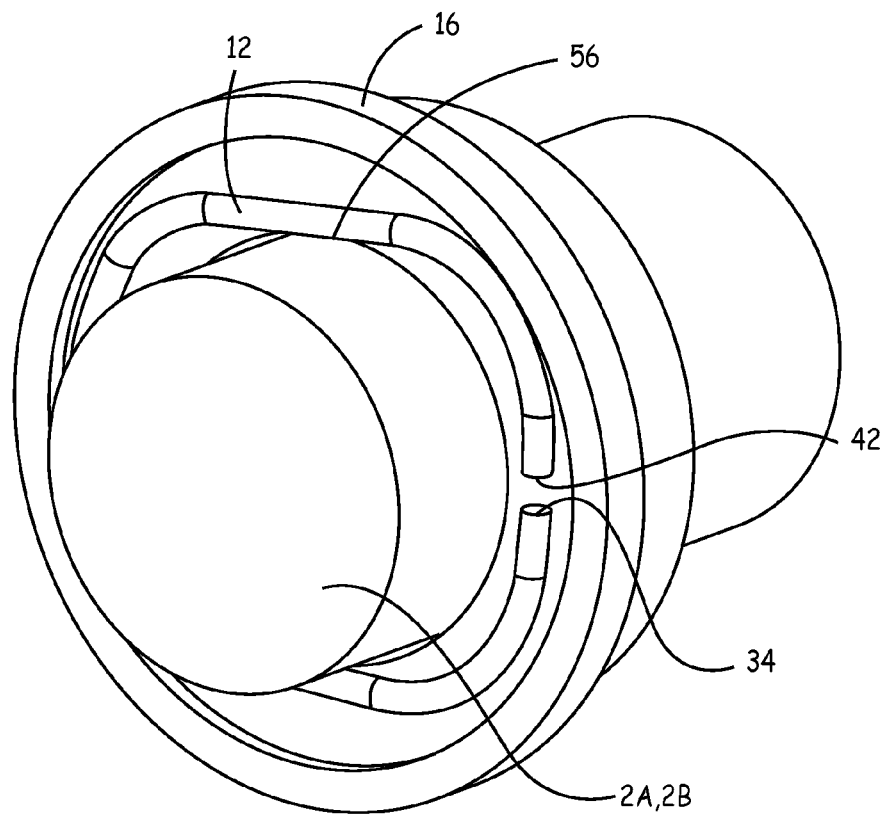
FIG. 7 is a schematic diagram of a housing of a connector assembly, according to an embodiment of the present invention, with a lead inserted therein.

FIG. 7 is a schematic diagram of a housing of a connector assembly, according to an embodiment of the present invention, with a lead inserted therein. While FIG. 7 illustrates connector clip 12 positioned within male member 16 and having lead 2A or 2B inserted therein, it is understood that when connector assembly is fully assembled, as in FIGS. 5A-5C, lead 2A or 2B advances through both female member 14 and male 16, and connector clip 12 in both female member 14 and male member 16 is advanced from the partially deflected position to the fully deflected position as described in reference to FIG. 7, although only male member 16 is illustrated in FIG. 7 for brevity sake.

As illustrated in FIGS. 6 and 7, when a physician or other user of the device wishes to establish an electrical connection between electrical lead 2A or 2B and the electrical source, the physician need merely place contact areas 8 of electric lead 2A or 2B within connector cavity 36 by inserting lead 2A or 2B within connector port 3 of connector block 7 (FIG. 1). Contact area 8A or 8B is then urged into connector cavity 36, where contact areas 8 come in contact with and push against contact points 56 of each connector clip 12 of connector assembly 10 of the present invention. As lead 2A or 2B is inserted within connector cavity 36 of connector block 7, lead 2A or 2B advances through aperture 18, and engages against contact points 56 causing spring arms 20 and 22 of connector clip 12 to be deflected yet further from the partially deflected position of FIGS. 3C and 3D so that end 34 is advanced a distance away from and no is longer engaged against end 44 of connector clip 12, placing connector clip 12 in the fully deflected position illustrated in FIG. 7. As a result, the spring force of connector clip 12 is transferred from being engaged at a point of contact between end 34 and end 44 of respective spring arms 20 and 22 of connector clip 12 to being against contact areas 8 of lead 2A or 2B. In this way, contact point 56 of each spring arm 20 and 22 is engaged against contact areas 8, causing the spring force to be applied by spring arms 20 and 22 against inserted contact areas 8, creating a secure electrical connection at contact points 56. Once fully inserted, electrical lead 2A or 2B is in a loaded state and will remain in place, connected to the electrical source.

Lead 2A or 2B may optionally be provided with grooves (not shown) positioned at expected contact points 56 that serve to further secure lead 2A or 2B when connector clip 12 expands into the space of the groove.

Figure 8A:
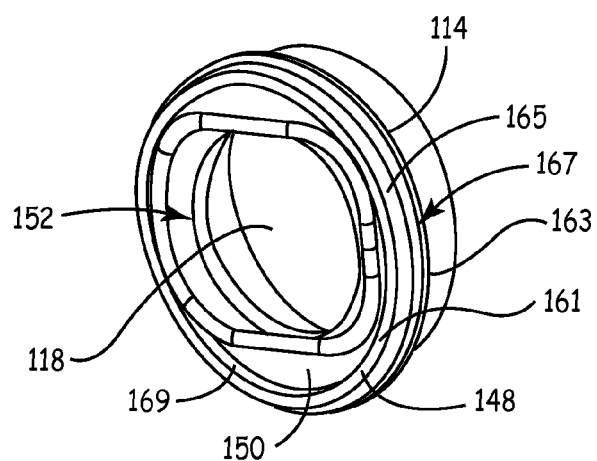
FIG. 8A is a schematic diagram of a female member of a housing of a connector assembly according to an alternate embodiment of the present invention.
Figure 8B:
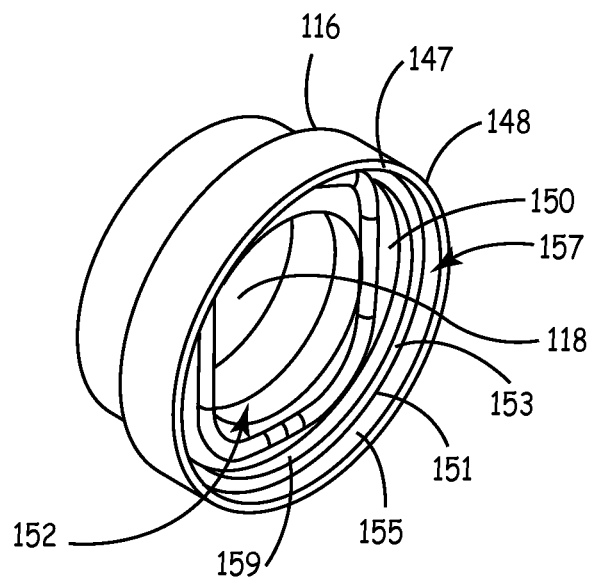
FIG. 8B is a schematic diagram of a male member of a housing of a connector assembly according to an alternate embodiment of the present invention.

FIG. 8A is a schematic diagram of a female member of a housing of a connector assembly according to an alternate embodiment of the present invention. FIG. 8B is a schematic diagram of a male member of a housing of a connector assembly according to an alternate embodiment of the present invention. As illustrated in FIGS. 8A and 8B, similar to male member 16 and female member 14 of connector assembly 10 described above, a female member 114 and a male member 116 of a housing portion 113 of a connector assembly 110 according to an alternate embodiment of the present invention are formed to be generally circular in shape, forming a circular central aperture 118 of sufficient size to accept proximal ends 9A or 9B of leads 2A and 2B. Therefore, embodiments of the present invention include aperture 118 having a diameter in a range of approximately 0.05-0.25 inches, although any sized diameter could be chosen. In one embodiment, for example, aperture 118 has a diameter of approximately 0.13 inches. However, female member 114 and male member 116 differ from female member 14 and male member 16 in that, as illustrated in FIG. 8B, in addition to an outer rim of male member 116 forming an outer annular flange 148 having a top portion 147 that extends outward from a front surface 150, male member 116 includes an inner flange 151 having a top portion 153 extending outward from front surface 150 a distance less than a length of a side wall 155 of outer flange 148 so that top portion 153 of inner flange 151 is positioned adjacent to side wall 155 of outer flange 148. As a result, top portion 153 of inner flange 151 and side wall 155 of outer flange 148 form a lip 157. In addition, aperture 118 is formed by front surface 150 and a side wall 159 of inner flange 151 extending from front surface 150 to top portion 153 so that side wall 159 and front surface 150 form a recessed portion 152 in which connector clip 12 is positioned while in the partially deflected position of FIGS. 3C and 3D, with top portion 26 of connector clip 12 positioned against side wall 159 of inner flange 151, as described above, using known welding techniques. Partially deflected connector clip 12 is positioned within recessed portion 152 so that side portion 28 of spring arm 20 and side portion 36 of spring arm 22 extend over aperture 118, and both lower curved portion 30, straight bottom portion 32 and end 34 of spring arm 20 and lower curved portion 38, straight bottom portion 40 and end 42 of spring arm 22 are spaced a distance from side wall 159 to enable connector clip 12 to be advanced from the partially deflected position to a fully deflected position, as described above, when the lead 2 is advanced through housing 113.

As illustrated in FIG. 8A, similar to female member 14 described above, female member 114 of the alternate embodiment includes an annular flange 148, having a top portion 161 that extends outward from front surface 150 of female member 114. However, flange 148 of female member 114 is spaced inward from an outer rim 163 so that a portion of front surface 150 between outer rim 163 and flange 148 of female member 114 and an outer side wall 165 of flange 148 form a lip 167. In addition, aperture 118 is formed by front surface 150 and an inner side wall 169 of flange 148 extending from front surface 150 to top portion 161 so that side wall 169 and front surface 150 form recessed portion 152 in which connector clip 12 is positioned while in the partially deflected position of FIGS. 3C and 3D, with top portion 26 of connector clip 12 positioned against side wall 169 of flange 148, as described above, using known welding techniques. Partially deflected connector clip 12 is positioned within recessed portion 152 so that side portion 28 of spring arm 20 and side portion 36 of spring arm 22 extend over aperture 118, and both lower curved portion 30, straight bottom portion 32 and end 34 of spring arm 20 and lower curved portion 38, straight bottom portion 40 and end 42 of spring arm 22 are spaced a distance from side wall 169 to enable connector clip 12 to be advanced from the partially deflected position to a fully deflected position, as described above, when the lead 2 is advanced through housing 113.

Figure 9A:
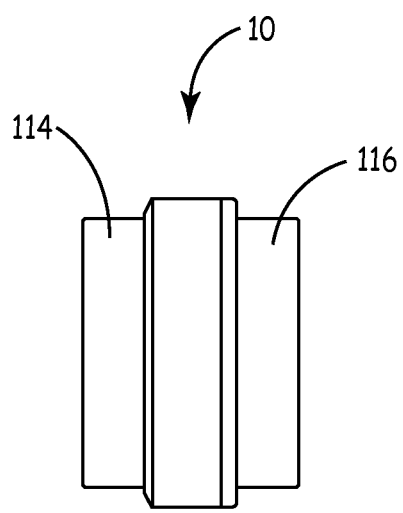
FIG. 9A is a side view of an assembled housing of a connector assembly according to an alternate embodiment of the present invention.
Figure 9B:
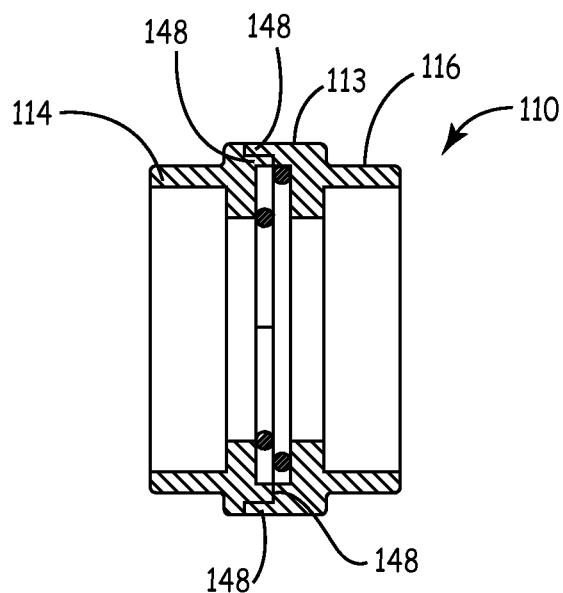
FIG. 9B is a cross-section side view of the assembled housing of the connector assembly of FIG. 9A.

FIG. 9A is a side view of an assembled housing of a connector assembly according to an alternate embodiment of the present invention. FIG. 9B is a cross-section side view of the assembled housing of the connector assembly of FIG. 9A. As illustrated in FIGS. 9A and 9B, once the desired number of connector clips 12 have been positioned within female member 114 and male member 116 of housing 113 as described above, top portion 147 of outer flange 148 of male member 116 is aligned with and fixedly positioned within lip 167 of female portion 114 and top portion 161 of flange 148 of female member 114 is positioned within lip 157 of male member 116 using known welding techniques, such as laser beam welding, for example, to form a fully assembled connector assembly 10 that creates a barrier against leakage of fluid through connector assembly 10 into the implantable medical device 1. It is understood that while welding techniques are described as being utilized to fixedly position female member 11 within female member 114, other fixation mechanisms may also be utilized. For example, top portion 147 of outer flange 148 of male member 116 may be aligned with and fixedly positioned within lip 167 of female portion 114 and top portion 161 of flange 148 of female member 114 may be aligned with and positioned within lip 157 of male member 116 using a press fit mechanism or threaded portions located along flange 148 of female member 114 and flange 148 of male member 116.

Figure 9C:
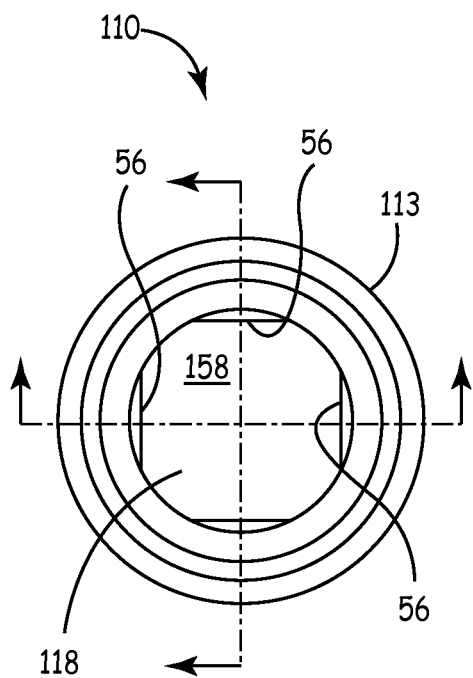
FIG. 9C is a top view of an assembled connector assembly according to an alternate embodiment of the present invention.

Finally, FIG. 9C is a top view of an assembled connector assembly according to an alternate embodiment of the present invention. As illustrated in FIG. 9C, similar to connector assembly 10 described above, in connector assembly 110 of the alternate embodiment of the present invention, contact points 56 of connector clip 12 positioned within female member 114 and of connector clip 12 positioned within male member 116 forming housing 113 of assembled connector assembly 110 are visible where connector clip 12 extends within aperture 118 created by housing 113, with aperture 118 of female member 114 and male member 116 of housing 113 overlapping in fluid communication to form an opening 158 for receiving a lead with spring arm 20 and spring arm 22 in the partially deflected position so that lead comes in contact with spring arm 20 and spring arm 22 at contact points 56. Once assembled, connector assembly 110 according to the alternate embodiment of the present invention operates in the same manner as assembled connector assembly 10 described above, and will not be repeated for the sake of brevity.

It is apparent from the foregoing discussion that the embodiments of the present invention illustrated in FIGS. 1-9C provides an improved connector assembly 10 or 110 for detachably connecting contact areas 8 of electrical lead 2A or 2B to an electrical apparatus. Since connector clips 12 are positioned within housing 13 or 113 in a partially deflected configuration, a constant force is exerted over the range of deflection of connector clip 12. Furthermore, since only a small deflection is necessary to create a significant force of retention, connector assembly 10 or 110 makes efficient use of the axial space on contact areas 8, allowing it to be very compact. Connector assembly 10 or 110 readily accepts insertion of contact areas 8, without the use of tools, and applies even force through connector clips 12 to maintain a constant electrical contact with an electrical lead that is not subject to varying impedance.

Although the invention has been described with reference to particular embodiments, it is to be understood that such embodiments are merely illustrative of the application of the principles of the invention. Numerous modifications may be made therein, and other arrangements may be devised, without departing from the true scope and spirit of the invention.

The invention claimed is:

1. A connector assembly for detachably connecting a lead to an implantable medical device, comprising:
   a connector block having a connector port to receive a proximal end of a lead inserted therein along an insertion axis of orientation;
   a first deflectable connector clip having only two lead contact surfaces including a first arm, a second arm, and a top portion extending between the first arm and the second arm, the connector clip capable of being deflected, prior to insertion of the lead, from a first position corresponding to a first relative position of the first arm and the second arm to a second position corresponding to a second relative position of the first arm and the second arm;
   a housing mounted within the connector block configured to maintain the first deflectable connector clip; and
   a second deflectable connector clip similar to the first deflectable connector clip, contained within the housing, rotated with respect to the first connector clip, wherein the housing is configured to maintain the first and second deflectable connector clips in the second position.

2. The assembly of claim 1, comprising:
   wherein the second deflectable connector clip includes two lead contact surfaces.

3. A connector assembly for detachably connecting a lead to an implantable medical device, comprising:
   a connector block having a connector port to receive a proximal end of a lead inserted therein along an insertion axis of orientation;
   a first deflectable connector clip having only two lead contact surfaces including a first arm, a second arm, and a top portion extending between the first arm and the second arm, the connector clip capable of being deflected, prior to insertion of the lead, from a first position corresponding to a first relative position of the first arm and the second arm to a second position corresponding to a second relative position of the first arm and the second arm; and
   a housing mounted within the connector block configured to maintain the first deflectable connector clip; and
   wherein the housing includes a first annular member and a second annular member, the first member formed to be fixedly engaged with the second member to form an aperture in alignment with the connector port to receive the lead proximal end along the insertion axis, the connector clip being enclosed within the housing, wherein the connector clip is positioned within one of the first member and the second member while in the second position, wherein the first arm extends from the top portion to a first end and the second arm extends from the top portion to a second end, and wherein the connector clip includes a first side wall along the first end and a second side wall along the second end, the end of the first arm and the end of the second arm being offset and partially overlapping so that the first side wall is adjacent to and engaged against the second side wall when the connector clip is in the first position, and the first arm and the second arm being partially spread apart so that the ends are non-overlapping and aligned so that the first end abuts the second end and the first side wall is not adjacent to and engaged against the second side wall when the connector clip is in the second position, the connector clip being oriented perpendicular to the insertion axis of orientation of the proximal end of a lead such that the arms, the non-overlapping ends of the arms, and the top portion together circumscribe an opening through which the proximal end of a lead passes during insertion.

* * * * *